Figure 1:
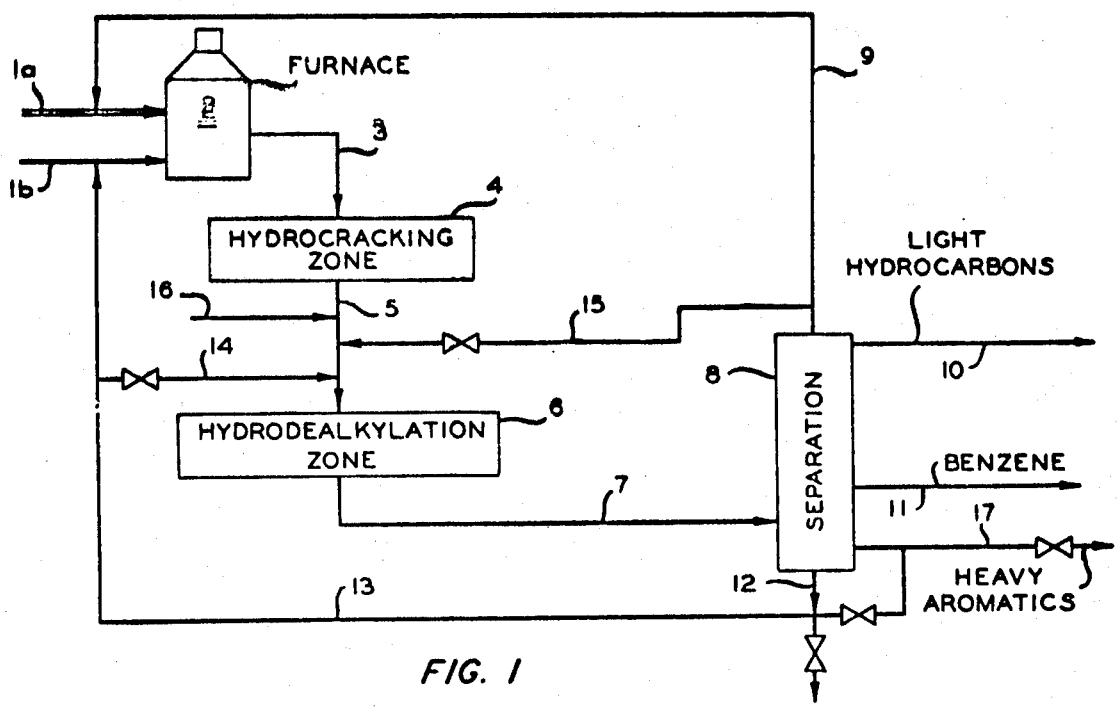

United States Patent [19]

Myers et al.

[11] 3,963,794

[45] June 15, 1976

[54] PRODUCTION OF BENZENE

[75] Inventors: John W. Myers; William C. Lanning, both of Bartlesville, Okla.

[73] Assignee: Phillips Petroleum Company, Bartlesville, Okla.

[22] Filed: Dec. 7, 1965

[21] Appl. No.: 512,100

Related U.S. Application Data

[63] Continuation-in-part of Ser. No. 121,016, June 30, 1961, Pat. No. 3,296,323.

[52] U.S. Cl. .......................... 260/672 NC; 208/95; 208/102; 208/107; 260/674 H
[51] Int. Cl. .......................... C07c 3/58; C07c 15/04
[58] Field of Search .................................... 260/672

[56] References Cited
UNITED STATES PATENTS

| | | | |
|---|---|---|---|
| 2,381,522 | 8/1945 | Stewart | 260/672 |
| 2,396,761 | 3/1946 | Tilton | 260/672 |
| 2,674,635 | 4/1954 | Beckberger | 260/672 |
| 2,907,800 | 10/1959 | Mertes | 260/672 |
| 2,929,775 | 3/1960 | Aristoff et al. | 260/672 |
| 3,160,671 | 12/1964 | Feigelman et al. | 260/672 |

FOREIGN PATENTS OR APPLICATIONS 712,440   7/1954   United Kingdom.................. 260/672

OTHER PUBLICATIONS

Silsby and Sawyer, "Dealkylation of Hydrocarbons," J. Applied Chemistry, pp. 347–356 (Aug. 6, 1956).

Primary Examiner—Delbert E. Gantz
Assistant Examiner—G. E. Schmitkons

[57] ABSTRACT

Benzene yields from hydrodealkylation of alkylaromatics are improved by adding diphenyl to the feed hydrocarbon stream.

4 Claims, 2 Drawing Figures

PRODUCTION OF BENZENE

This application is a continuation-in-part of Ser. No. 121,016, filed June 30, 1961, now U.S. Pat. No. 3,296,323.

This invention relates to production of benzene. In one aspect, this invention relates to a process and apparatus for producing benzene which comprises passing a feed stream comprising a major proportion of alkyl aromatic compounds along with a minor proportion of non-aromatic compounds in the presence of added hydrogen to a refractory reaction zone, heating the feed stream in the reaction zone to a temperature of at least about 1,100°F, and recovering a benzene-containing stream from the zone. In another aspect, the invention relates to a process and apparatus for hydrodealkylating a stream comprising alkyl aromatic compounds having at most about six alkyl carbon atoms per molecule which comprises passing the stream, heated to a temperature of at least about 1,100°F, in the presence of added hydrogen and a minor proportion of non-aromatic hydrocarbons to a reaction zone and recovering from the zone a benzene-containing stream. In still another aspect, this invention relates to a process and apparatus for producing benzene which comprises passing a feed stream comprising alkyl aromatic compounds having at most about six alkyl carbon atoms per molecule to a pre-heating zone, heating the feed stream in the preheating zone to a temperature of at most about 1,200°F, recovering the effluent from the preheating zone and passing said effluent to a refractory reaction zone, heating the effluent in the refractory reaction zone, and recovering from the refractory reaction zone a benzene-containing stream. In yet another aspect, the invention relates to a process and apparatus for hydrodealkylating a stream comprising alkyl aromatic compounds having at most about six alkyl carbon atoms per molecule which comprises passing the stream to a pre-heating zone in the presence of a minor proportion of non-aromatic compounds and added hydrogen, heating the stream in the pre-heating zone by substantial hydrocracking of the non-aromatic compounds to a temperature of at most about 1,200°F, recovering the effluent from the pre-heating zone and passing the effluent to a refractory reaction zone, heating the effluent in the refractory reaction zone to a temperature in the range of from about 1,100°F to about 1,500°F, recovering from the reaction zone a second effluent stream, separating the second effluent stream into a first benzene-containing product fraction and a second heavy fraction boiling above about 500°F, and returning the second heavy fraction to the process. In still aspect, this invention relates to a process and apparatus for thermal hydrodealkylation of a feed stream comprising alkyl aromatic compounds which comprises passing said feed stream in the presence of added hydrogen to a reaction zone in which hydrodealkylation causes heating of said feed stream in said reaction zone, passing the resulting hydrodealkylated stream to a separation zone, recovering from said separation zone a hydrodealkylated product and a heavy ends product, returning at least a portion of said heavy ends product to said feed stream and adding to the returned portion sufficient non-aromatic compounds to maintain the rate of hydrodealkylation at least as high as it would be under similar hydrodealkylation conditions in the absence of said step of returning.

As is known in the art, various processes have been utilized in the past for preparation of benzene and for hydrodealkylation of an alkyl aromatic stream. In catalytic processes, there are encountered the usual operational and cost difficulties of preparing and maintaining an active catalyst bed. Further, at the temperatures prevailing in a reaction of this type, there is often prevalent the problem of "dusting" of the interior of the reactor surface. This "dusting" of the reactor surface results in degradation and eventual failure of the reactor, and is thought to be caused possibly partly by the presence of both hydrogen and hydrocarbons at the temperatures involved.

Thus, it is an object of this invention to provide a method and apparatus suitable for non-catalytic preparation of benzene from alkyl benzenes. It is another object of this invention to provide a method and apparatus for non-catalytic hydrodealkylation of alkyl aromatic compounds. It is another object of this invention to provide a two-step process and apparatus for preparation of benzene wherein the second or high-temperature step is carried out in a reactor which is not subject to degradative "dusting." It is still another object of this invention to provide a process and apparatus for production of benzene wherein a portion of the preheating of the charge necessary for the thermal hydrodealkylation of the alkyl benzene portion of the feed is provided by the exothermic hydrocracking of non-aromatic compounds also present in the feed. It is another object of this invention to provide a process in which non-aromatic compounds are added with the aromatic feed to the hydrodealkylating step and hydrodealkylation rates are increased. It is still another object of this invention to provide a process in which heavy aromatic products are recycled and non-aromatic hydrocarbons are added in the proper amount so that the hydrodealkylating rate is at least as high as with the pure aromatic feed.

Figure 2:
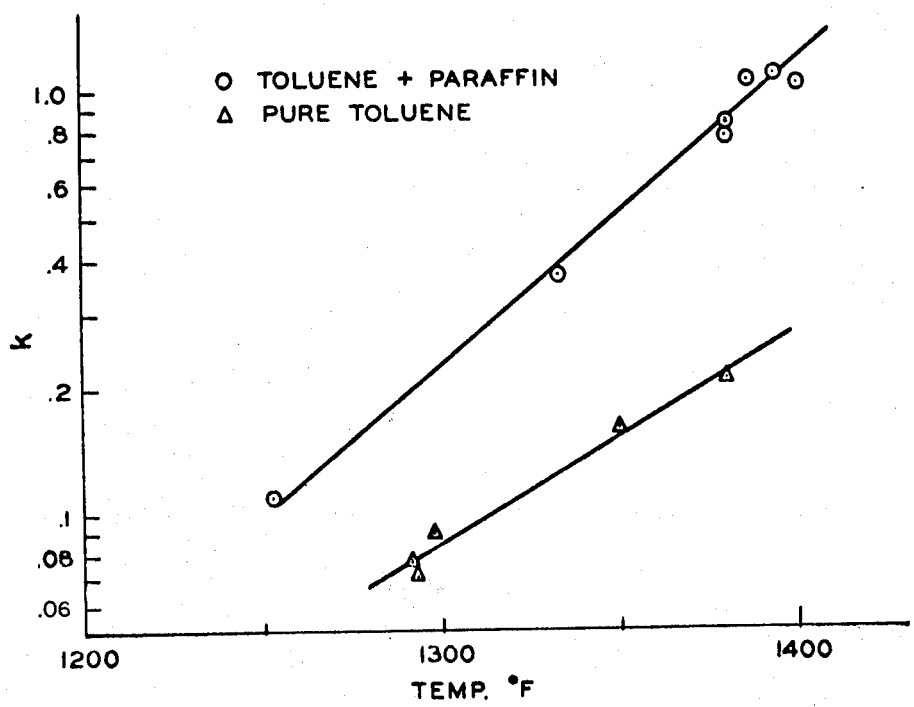

Other aspects, objects, and the several advantages of the invention will become apparent upon study of the disclosure, the claims appended thereto, and the accompanying drawing in which:

FIG. 1 is a schematic flow representation of one embodiment of our invention, and FIG. 2 is a graph showing the effect of inclusion of paraffins in the hydrodealkylation feed.

We have further discovered that the hydrodealkylation efficiency can be increased by the addition of biphenyls to the feed. The biphenyls can be obtained as a by-product in the hydrodealkylation operation or can be supplied from an independent source. The biphenyls can be added to the feed with or without the addition of non-aromatics.

We have now discovered that the above objects can be accomplished by a process and apparatus wherein a portion of the heat necessary for hydrodealkylation of alkyl aromatic compounds is furnished by the hydrocracking of a minor proportion of non-aromatic compound at temperatures lower than those at which substantial hydrodealkylation occurs. We have further discovered that undesirable "dusting" of the hydrodealkylation reactor interior surface can be prevented by carrying out the hydrodealkylation reaction within a refractory reaction zone. Although the entire process of our invention can be carried out in a single reaction zone, we have further discovered that a pre-heating of the alkyl aromatic compounds can be advantageously effected by preliminary hydrocracking of a non-aromatic portion of the feed streeam in a preheating zone, followed by hydrodealkylation of the alkyl aromatic content of the stream in a refractory rection zone. We have further discovered that addition of non-aromatic hydrocarbon to the feed increases hydrodealkylation rates and that recycle of heavy aromatic products reduces these rates although such recycle increases overall hydrodealkylation efficiency. Moreover, the proper amount of non-aromatic hydrocarbon can be added with the feed to at least compensate for the reduction caused by recycle of heavy aromatic products.

Referring now to the drawings, and to FIG. 1 in particular, a hydrocarbon feed containing 80 to 95 weight percent alkylaromatics and 5 to 20 weight percent paraffins, naphthenes and/or olefins is charged to furnace 2 through line 1b and hydrogen is charged to this furnace through line 1a. These materials are pre-heated in the furnace and passed through line 3 to hydrocracking zone 4, in which non-aromatics are hydrocracked, either thermally or catalytically, the exothermic heat of reaction serving to complete the pre-neating to thermal hydrodealkylation temperature for the alkylaromatics. The effluent from zone 4 is conducted by way of line 5 to hydrodealkylation zone 6, in which the alkylaromatics are converted to produce benzene. The reactor defining zone 6 is preferably a steel shell provided with an internal refractory lining providing insulation to prevent loss of heat. External insulation can also be provided.

The effluent from zone 6 is conducted by line 7 to separation zone 8, which can comprise, for example, suitable absorbers and fractionators well known in the art. Hydrogen is removed through line 9 and is recycled to line 1a for reuse. Light hydrocarbons boiling below benzene are removed through line 10 to be utilized in any desired manner. Benzene is removed through line 11 as a product of the process, and is conducted to storage, not shown. Heavy ends comprising unconverted alkylbenzenes are removed from zone 8 through line 12; and these are ordinarily recycled through line 13 and line 1b, although they can be removed through line 12 by use of the valving provided. All or a portion of the stream in line 13 can be passed by way of lines 14 and 5 to zone 6, but recycling by way of line 1b is preferred.

Because the hydrocracking reaction consumes hydrogen, hydrogen can be added to line 5 through line 15 to replace part or all of the hydrogen consumed in hydrocracking zone 4 and maintain the desired ratio of hydrogen and hydrocarbon in zone 6 without the hydrogen necessary for this passing through the hydrocracking zone.

Usually, a relatively small amount of heavy aromatics, which is predominantly biphenyl or alkylated biphenyl, is made in the hydrodealkylation step. This can be removed from the separation zone through line 17 or it can be recycled through line 13, by use of the valving provided, with the unconverted feed. At times, it may be necessary to separate a biphenyl concentrate from these heavy products and to recycle only the biphenyl concentrate. When this heavy aromatic product is recycled, overall hydrodealkylation efficiencies are increased but rates are decreased. This reduction can be compensated for by addition of non-aromatic hydrocarbon, for example, through line 16. In one embodiment, the beneficial effect of the addition of non-aromatic to increase hydrodeallylation rates can be used in a one-step process without a preliminary hydrocracking step. It is obvious to one skilled in the art that the hydrodealkylation efficiencies can be increased by supplying biphenyl concentrate from other sources to the feed to the hydrodealkylation operation and need not be limited to recycling biphenyl concentrate from heavy products from the hydrodealkylation process.

Referring now to FIG. 2, there is shown the effect of the inclusion of paraffins in the hydrodealkylation feed. This graph is a compilation of the runs in the following two specific examples.

EXAMPLE I

TABLE I
EFFECT OF TEMPERATURE AND PRESSURE ON HYDRODEALKYLATION OF TOLUENE CONCENTRATE[1]

| Run No. | 1 | 2 | 3 | 4 | 5 | 6 | 7 |
|---|---|---|---|---|---|---|---|
| Process Conditions | | | | | | | |
| Temperature, °F | 1253 | 1333 | 1380 | 1379 | 1386 | 1394 | 1399 |
| Pressure, psig | 605 | 600 | 500 | 500 | 500 | 500 | 300 |
| Time, sec. | 43.6 | 13.7 | 5.9 | 8.3 | 3.6 | 3.6 | 5.3 |
| LHSV | 1.0 | 3.0 | 5.4 | 4.3 | 9.0 | 9.0 | 3.8 |
| $H_2$/feed, mol ratio | 3.8 | 4.0 | 4.2 | 3.6 | 4.1 | 4.1 | 4.1 |
| Reactor effluent composition[2], wt.% | | | | | | | |
| Methane | 18.7 | 19.2 | 18.4 | 19.6 | 17.0 | 17.3 | 18.0 |
| Ethane | 4.3 | 4.5 | 4.4 | 4.2 | 4.5 | 4.3 | 4.2 |
| Propane | trace | trace | trace | trace | trace | trace | trace |
| Benzene | 66.0 | 66.5 | 65.4 | 66.4 | 60.6 | 62.9 | 62.7 |
| Toluene | 6.5 | 5.1 | 6.8 | 3.6 | 13.2 | 10.8 | 10.0 |
| Xylene | 0.2 | trace | 0.2 | 0.1 | 0.5 | 0.2 | 0.3 |
| Heavies (above 350°F) | 4.3 | 4.7 | 4.8 | 6.1 | 4.2 | 4.5 | 4.8 |
| Total | 100.0 | 100.0 | 100.0 | 100.0 | 100.0 | 100.0 | 100.0 |
| Reactor effluent yield, wt. % of HC feed | 101.4 | 101.2 | 101.1 | 101.2 | 100.4 | 100.0 | 100.9 |
| Recovery, weight percent | 98.9 | 98.5 | 98.3 | 98.4 | 98.0 | 97.7 | 98.6 |
| Aromatic conversion, % | 92.7 | 95.4 | 92.4 | 95.9 | 85.2 | 88.1 | 88.8 |
| Dealkylation efficiency[3], % | 92.6 | 91.2 | 91.5 | 89.5 | 91.6 | 91.4 | 91.3 |
| Ultimate yield of heavies, wt. % | 5.1 | 5.4 | 5.7 | 6.8 | 5.3 | 5.4 | 5.8 |
| Estimated recycle dealkylation efficiency [4] | 95.7 | 94.2 | 94.8 | 93.5 | 94.7 | 94.6 | 94.7 |
| Toluene rate constant k [5], sec$^{-1}$ (mol/liter)$^{-\frac{1}{2}}$ | 0.11 | 0.37 | 0.86 | 0.79 | 1.06 | 1.14 | 1.04 |
| Acid wash color of benzene before clay treating | | 3− | 6 | 4 | 4 | 4 | 4+ |

[1] Weight percent composition: non-aromatics (principally dimethylhexanes) 6.4; toluene 83.6; xylene 9.1; $C_9$+ aromatics 0.9.
[2] Calculated on a hydrogen-free basis.
[3] Dealkylation efficiency was calculated from recovery figures rather than on a no-loss basis. Thus the calculated figures are conservative.
[4] It was assumed that recycling heavy aromatics would have the same effect as conversion of 70 percent of the diphenyl to benzene.
[5] The toluene reaction was considered to be first order with respect to aromatic concentration and with rate constant proportional to square root of average hydrogen concentration. This method of handling hydrogen concentration facilitates calculations and gives about the same results as considering the reaction half order with respect to hydrogen.

EXAMPLE II

TABLE II
HYDRODEALKYLATION OF PURE TOLUENE

| Run No. | 8 | 9 | 10 | 11 | 12 |
|---|---|---|---|---|---|
| Process Conditions | | | | | |
| Temperature, °F | 1298 | 1293 | 1292 | 1350 | 1387 |
| Pressure, psig | 500 | 500 | 500 | 500 | 500 |
| Time, sec. | 65.4 | 77.5 | 49.5 | 36.7 | 18.2 |
| LHSV | 0.52 | 0.45 | 0.69 | 0.91 | 1.78 |
| $H_2$/feed, mol ratio | 4.0 | 3.8 | 3.9 | 3.9 | 4.0 |
| Reactor effluent composition[1], wt. % | | | | | |
| Methane | 16.2 | 16.3 | 15.4 | 16.8 | 14.8 |
| Ethane | 0.6 | 0.4 | 0.4 | 0.5 | 0.5 |
| Propane | 0.0 | 0.0 | 0.0 | 0.0 | 0.0 |
| Benzene | 75.4 | 73.7 | 70.6 | 73.9 | 68.4 |
| Toluene | 3.6 | 4.7 | 9.9 | 3.9 | 12.3 |
| Xylene | trace | 0.0 | trace | trace | trace |
| Heavies (above 350°F) | 4.2 | 4.8 | 3.7 | 4.9 | 4.0 |
| Total | 100.0 | 100.0 | 100.0 | 100.0 | 100.0 |
| Reactor effluent yield, wt. % of HC feed | 100.7 | 101.1 | 101.7 | 102.0 | 102.8 |
| Recovery, wt. % | 98.6 | 98.6 | 99.9 | 99.9 | 101.0 |
| Toluene conversion, % | 96.4 | 95.3 | 89.9 | 96.0 | 87.4 |
| Dealkylation efficiency[2], % | 92.7 | 92.4 | 94.0 | 92.6 | 94.9 |
| Ultimate yield of heavies, wt. % | 4.5 | 5.2 | 4.3 | 5.2 | 4.7 |
| Estimated recycle dealkylation efficiency[3], % | 95.7 | 95.9 | 96.3 | 96.0 | 97.7 |
| Toluene rate constant $k^{[4]}$, sec$^{-1}$ (mol/liter)$^{-1/2}$ | 0.09 | 0.07 | 0.08 | 0.16 | 0.21 |

[1] Calculated on a hydrogen-free basis.
[2] Dealkylation efficiency was calculated from recovery figures rather than on a no-loss basis. Thus the calculated figures are conservative.
[3] It was assumed that recycling heavy aromatics would have the same effect as conversion of 70 percent of the diphenyl to benzene.
[4] The hydrodealkylation reaction was considered to be first order with respect to toluene concentration and with rate constant proportional to square root of average hydrogen concentration. This method of handling hydrogen concentration facilitates calculations and gives about the same results as considering the reaction half order with respect to hydrogen.

The following runs show the effect of feed dilution.

EXAMPLE III

TABLE III
EFFECT OF HYDROGEN AND METHANE DILUTION ON HYDRODEALKYLATION OF TOLUENE CONCENTRATE[1]

| Run No. | 13 | 14 | 15 | 16 | 17 |
|---|---|---|---|---|---|
| Process Conditions | | | | | |
| Temperature, °F | 1253 | 1256 | 1256 | 1254 | 1286 |
| Pressure, psig | 605 | 600 | 600 | 600 | 600 |
| Time, sec. | 43.6 | 33.7 | 40.3 | 64.2 | 47.8 |
| LHSV | 1.0 | 0.69 | 0.58 | 0.37 | 0.48 |
| $H_2$/feed, mol ratio | 3.8 | 8.2 | 4.1 | 4.0 | 4.3 |
| Methane/feed, mol ratio | 0.0 | 0.0 | 4.1 | 4.0 | 4.3 |
| Reactor effluent composition[2], wt. % | | | | | |
| Methane | 18.7 | 19.6 | 50.4 | 50.7 | 51.1 |
| Ethane | 4.3 | 4.9 | 2.8 | 2.8 | 2.9 |
| Propane | trace | trace | 0.6 | trace | trace |
| Benzene | 66.0 | 69.6 | 35.6 | 38.6 | 40.1 |
| Toluene | 6.5 | 4.1 | 8.2 | 5.6 | 3.1 |
| Xylene | 0.2 | trace | 0.3 | 0.2 | 0.1 |
| Heavies (above 350°F) | 4.3 | 1.8 | 2.1 | 2.1 | 2.7 |
| Total | 100.0 | 100.0 | 100.0 | 100.0 | 100.0 |
| Reactor effluent yield, wt. % of HC feed | 101.4 | 101.4 | 101.3 | 99.5 | 100.6 |
| Recovery, wt. % | 98.9 | 98.7 | 99.7 | 98.3 | 99.1 |
| Aromatic conversion, % | 92.7 | 95.5 | 84.4 | 89.6 | 94.0 |
| Dealkylation efficiency[3], % | 92.6 | 95.1 | 92.8 | 92.5 | 92.8 |
| Ultimate yield of heavies, wt. % | 5.1 | 2.1 | 4.4 | 4.8 | 6.0 |
| Estimated recycle dealkylation efficiency[4], % | 95.7 | 96.3 | 95.4 | 95.3 | 96.3 |
| Toluene rate constant $k^{[5]}$, sec$^{-1}$ (mol/liter)$^{-1/2}$ | 0.11 | 0.15 | 0.11 | 0.08 | 0.14 |
| Xylene rate constant $k^{[5]}$, sec$^{-1}$ (mol/liter)$^{-1/2}$ | 0.16 | 0.20 | 0.16 | 0.11 | 0.17 |

[1] Weight percent composition: non-aromatics (principally dimethylhexanes) 6.4; toluene 83.6; xylene 9.1; $C_9$+ aromatics 0.9.
[2] Calculated on a hydrogen-free basis.
[3] Dealkylation efficiency was calculated from recovery figures rather than on a no-loss basis. Thus the calculated figures are conservative.
[4] It was assumed that recycling heavy aromatics would have the same effect as conversion of 70 percent of the diphenyl to benzene.
[5] The toluene and xylene reactions were both considered to be first order with respect to aromatic concentration and with rate constant proportional to square root of average hydrogen concentration. This method of handling hydrogen concentration facilitates calculations and gives about the same results as considering the reaction half order with respect to hydrogen.

In the foregoing examples, the mole percentage of heavies in the effluent varied from about 1 percent (Run 14) to about 3 percent (Run 4). The recycle dealkylation efficiency was calculated from the ultimate yield of heavies on the basis that the heavies contained about 70 weight percent biphenyl. Thus, the biphenyl for recycle varied from about 1 to 3 percent of the liquid hydrocarbon charge. Dealkylation efficiency is on a toluene mole basis so that a yield of 84.8 pounds of benzene from 100 pounds of toluene feed would be 100 percent mole efficiency.

In the runs of the preceding three tables, the tests at 1,300°F and lower temperatures were conducted in empty 2- and 3-foot sections of 1-inch schedule 80 A.I.S.I. type 310 stainless steel pipe. A quartz-lined pipe was used in most of the higher temperature tests. Carbon deposition was low. After a 96-hour test at 1,253°F (92.7 percent conversion level), carbon burned from the reaction pipe was equivalent to only 0.002 weight percent of the feed and no coke was observed carried from the reaction tube by the hydrocarbon.

The following runs were made to show that a non-aromatics in toluene concentrate is converted at lower temperatures than are aromatics (here, 6.4 weight percent non-aromatics in toluene concentrate).

EXAMPLE IV

TABLE IV
CONVERSION OF NON-AROMATICS IN TOLUENE CONCENTRATE

| Process Conditions | | | |
|---|---|---|---|
| Temperature, °F | 846 | 997 | 1169 |
| Pressure, psig | 310 | 310 | 305 |
| Time, sec. | 41.3 | 38.5 | 32.9 |
| LHSV | 0.76 | 0.75 | 0.76 |
| H$_2$/feed mol ratio | 3.7 | 3.6 | 3.7 |
| Conversion, % | | | |
| Non-aromatics | 2 | 57 | 100 |
| Toluene | 0 | 0 | 35 |

The product benzene had the following properties:

EXAMPLE V

TABLE V
SPECIFICATION TESTS ON BENZENE FRACTIONS

| Test | ASTM Designation | Samples[1] |
|---|---|---|
| Solidification point | D-852-47[2] | 5.35°C |
| Distillation | D-850-56 | 79.9–80.8°C |
| Sp. Gr. (15.56/15.56°C) | D-891-51 | 0.8848 |
| Color | D-853-47 | Acceptable |
| Acidity | D-847-47 | No free acid |
| Acid wash color | D-848-47 | (2–6), 0+[3] |
| Copper corrosion | D-130-56[4] | 1 (Sl. tarnish) |
| Sulfur compounds | D-853-47 | No H$_2$S, SO$_2$ |
| Thiophene | D-931-50 | <1 ppm |

[1] Four benzene fractions from products of runs at different temperatures were submitted for specification tests. These fractions constituted the total benzene cuts separated in a Hypercal column. Except in the acid-wash color test, all samples gave substantially the same results.
[2] Method D-1477-57T modified so as to be similar to D-852-47 was used.
[3] Acid wash colors varied from 2 to 6 before clay treating. Samples having 2 and 4 acid wash colors were clay treated. After treating, the colors were 0+.
[4] This is a more stringent test than D-849-47.

EXAMPLE VI

The following thermal tests were at 1,210°–1,340°F, 300 psig, with 3.5 mols of hydrogen per mol of toluene, and at about 15 seconds contact time. They were 2–3 hours in length. The reactor was packed with alpha alumina to increase the efficiency of heat transfer and reduce void space. At 1,210°F, conversion was only 19 percent but at 1,280°F and 1,340°F both conversion and efficiency were high:

| Temperature, °F | 1210 | 1280 | 1340 |
|---|---|---|---|
| Conversion, wt. % | 18.5 | 43.9 | 73.3 |
| Efficiency to C$_6$H$_6$, wt. % | 83.2 | 80.6 | 80.2 |
| Efficiency, % of theory | 98.1 | 95.0 | 94.6 |

Conversion to coke was of the order of 0.1 to 0.2 weight percent of the feed.

EXAMPLE VII

A mixture of 90 weight percent toluene and 10 percent n-octane is thermally hydrocracked at 300 psig with a hydrogen-to-hydrocarbon mol ratio of 4. The hydrogen and hydrocarbon are pre-heated and fed to a first reaction zone at an inlet temperature of 1,050°F. The contact time in this zone is 35 seconds. At the 1,050°F temperature, substantial amounts of the octane are exothermally hydrocrackked, whereas practically none of the toluene reacts. Approximately 85 percent of the octane is converted in this first zone and the outlet temperature is about 1,150°F. The effluent then enters a second zone at 1,150°F. The contact time in this zone is 60 seconds. At 1,150°F the toluene hydrodealkylates at fast enough rate to give additional temperature rise and the temperature increases from 1,150°F to about 1,390°F in this zone. The overall toluene conversion is about 90 percent.

The conditions for carrying out the hydrodealkylation reaction are as follows:

| Variable | Broad | Preferred |
|---|---|---|
| Temperature, °F | 1100–1500 | 1200–1400 |
| Contact time, sec. | 1–150 | 2–100 |
| Pressure, psig | 50–1000 | 100–600 |
| H$_2$/HC, mol | 1–20 | 1.5–10 |

EXAMPLE VIII

A test was made in which toluene concentrate containing 6.4 weight percent non-aromatics (about 80 percent paraffins and 20 percent naphthenes) mixed with 12 percent of heavy aromatics formed in previous tests was used as feed. Presence of these heavy aromatics increased hydrodealkylating efficiency as calculated from toluene conversion but also reduced rates:

| Feed | Toluene Concentrate Containing 6.4 wt.% Non-aromatics + 12% Heavy Aromatics | Toluene Concentrate | Pure Toluene |
|---|---|---|---|
| Temperature, °F. | 1329 | 1333 | 1350 |
| Pressure, psig | 600 | 600 | 500 |
| LHSV | 3.0 | 3.0 | 0.9 |
| $H_2$/feed, mol ratio | 4.1 | 4.0 | 3.9 |
| Dealkylation efficiency, % | 104.7 | 91.2 | 92.6 |
| Toluene rate constant, $sec^{-1}$ (mol/liter)–½ | 0.24 | 0.37 | 0.16 |

These data show that the 6.4 percent non-aromatics more than compensated for the reduction in rate caused by the heavy aromatics. Thus, if the amount of non-aromatics is equal to at least about half of the weight percent of heavy aromatics, the hydrodealkylation rate is at least as high as with pure toluene. FIG. 2 also shows how the non-aromatics increased hydrodealkylation rates.

In the above example, it is seen that the addition of heavy aromatics containing predominantly biphenyls or alkylated biphenyls increase the hydrodealkylation efficiency. The term "biphenyl" is used herein to designate compounds also called diphenyls. In general, the reaction conditions for the hydrodealkylation process in which biphenyls have been added to the feed are as follows:

| | |
|---|---|
| Hydrodealkylation temperature | 950–1450° F. |
| Pressure | 400 – 10,000 psig |
| time | 1 – 600 seconds |
| Mols of hydrogen per mol of normally liquid hydrocarbon charge | 1.0 – 20.0 |
| Mols of biphenyl per 100 mols of normally liquid hydrocarbon charge | 1 – 15 |
| Wt. percentage of non-aromatics in the feed based on normally liquid hydrocarbon charge | 5 – 20 |

In the foregoing example, it can be estimated that the heavy aromatics contained about 70 percent biphenyl so that the charge of biphenyl to the reaction zone was about 5 mol percent based on total mols of normally liquid hydrocarbon charge. In other words, there were about 5 mols of biphenyl per 100 mols of toluene + non-aromatics + heavy aromatics supplied to the reaction zone.

While in the foreegoing examples biphenyl mol percentages of 1–5 based on total liquid hydrocarbon charge have been used, the mol percentage of biphenyl hydrocarbons based on total liquid hydrocarbon charge to the reaction can vary from 1–15 as above set forth.

The rate of reaction is dependent on the temperature, pressure, and hydrogen concentration; and, therefore, these variables must all be controlled along with the reaction time in order to effect the desired depth of conversion.

The reaction is exothermic, and consequently temperature will increase in the direction of flow of the reactants in an adiabatic reaction zone. The average reaction temperature should be within the range given, although the maximum temperature can be outside these ranges.

Some savings in charge heating is effected by including a limited amount of non-aromatic hydrocarbons in the feed, these including normally liquid paraffins, cycloparaffins and olefins. These non-aromatics begin hydrocracking at a lower temperature than the aromatics, and the exothermic heat of reaction is used for pre-heating the other hydrocarbon reactants (aromatics) and the hydrogen in the stream up to a temperature sufficiently high to effect hydrodealkylation of the aromatics. These hydrocrackable non-aromatics are preferably present in an amount between 5 and 20 weight percent of the aromatic hydrocarbon in the feed. Less than 5 percent is not deleterious, but is not sufficient to make any really significant saving in heating cost. More than 20 percent of the hydrocrackable non-aromatics can result in excessive temperature rise. Thus, control of the non-aromatic portion of the feed within this range is beneficial. These non-aromatics are hydrocracked principally to normally gaseous paraffins and are advantageously separated from the effluent and used in firing the feed pre-heater. Thus, low octane $C_6$, $C_7$ and $C_8$ refinery streams can be used in this manner to reduce the temperature of the pre-heater, thus increasing furnace tube life, and the products of non-aromatic hydrocracking used as pre-heater fuel.

The conditions for carrying out the hydrocracking step are a feed temperature of 950°F to 1,150°F, preferably 1,000°F to 1,100°F, with the contact time, pressure and hydrogen/hydrocarbon mol ratio being within the same ranges as the hydrodealkylation reaction. This reaction is also exothermic and is dependent on temperature, pressure and hydrogen concentration, as well as reaction time. These varibales are controlled within the foregoing ranges to effect the final 50°F to 250°F. of heating of the reactant stream to a temperature in the range of 1,100°F to 1,200°F before entering the hydrodealkylation zone.

The alkylbenzenes used in this process are preferably those with less than six alkyl carbon atoms in the molecule. These are readily separated substantially free of polycyclics such as naphthalene, which polycyclics will not be converted to benzene in substantial amount.

One particular type of reaction vessel is quite advantageous in operating this process, this being a refractory lined steel vessel operated with the steel wall relatively cool. This is essentially an internally insulated vessel. Many of the types of steel commonly used in fabrication of reaction vessels, including 25–20 stainless, form dust upon use in hydrodealkylation. The use of internal insulation and a relatively cold shell avoids this difficulty.

Use of a controlled quantity of paraffins in the feed to generate heat within the reaction zone to furnish the high temperature portion of the pre-heating is quite advantageous in combination with this type of reaction vessel. Steel furnace tubes are also subject to the difficulty of dusting at high temperatures, and effecting the final heating by the hydrocracking paraffins within the refractory lined reaction vessel eliminates contact of the feed with the furnace tube walls in the most deleterious temperature range.

Although we have discussed our invention only in conjunction with a thermal, i.e., non-catalytic, process, we have further discovered that in another preferred embodiment the feed material comprising aromatic hydrocarbons with a minor proportion (as related to aromatic hydrocarbons) of a non-aromatic feed can be preheated so as to initiate cracking of the non-aromatic portion in a catalytic hydrocracking zone. This initial preheating is continued up to a temperature below where "dusting" of the reactor begins, and the material is then passed to a refractory lined thermal zone wherein additional exothermic hydrocracking of the non-aromatic portion furnishes a portion of the preheat necessary to thermally dealkylate the aromatic portion of the feed.

Reasonable variation and modification are possible within the scope of the disclosure, drawings, and appended claims to the invention, the essence of which is that there is provided a process and apparatus for production of benzene from a feed comprising a major proportion of alkyl aromatic compounds and a minor proportion of non-aromatic compounds wherein preheating of the feed is acccomplished by cracking of non-aromatics and wherein hydrodealkylation is carried out in a refractory lined reaction zone, and wherein the rate of hydrodealkylation in the presence of recycled heavy ends is maintained by addition of non-aromatic compounds, and wherein the hydrodealkylation efficiency can be improved by the addition of biphenyls.

We claim:

1. In a process for hydrodealkylating alkylated monocyclic aromatic hydrocarbons in an alkylated monocyclic aromatic-containing hydrocarbon fraction wherein such fraction is subjected to thermal conversion in a reaction zone devoid of catalytically active material in the presence of hydrogen at a temperature ranging from 950°F to 1,450°F at a pressure ranging from 400 pounds per square inch to 10,000 pounds per square inch for a time ranging from 1 second to 600 seconds with the amount of hydrogen ranging from 1.0 to 20.0 moles of hydrogen per mole of the normally liquid hydrocarbon charge, the improvement which comprises increasing the yield of recoverable monocyclic aromatic hydrocarbons by introducing diphenyl into the reaction zone together with the alkylated monocyclic aromatic-containing hydrocarbon fraction, said diphenyl being in an amount ranging from 1 mole percent to 15 mole percent based on the total moles of normally liquid hydrocarbon charge to the reaction zone, and recovering the monocyclic aromatic hydrocarbons.

2. In a process for hydrodealkylating alkylated monocyclic aromatic hydrocarbons in an alkylated monocyclic aromatic-containing hydrocarbon fraction wherein such fraction is subjected to thermal conversion in a reaction zone devoid of catalytically active material in the presence of hydrogen and at a temperature ranging from 1,100° to 1,500°F, at a pressure ranging from 50 psi to 1,000 psi for a time ranging from 1 second to 150 seconds with the amount of hydrogen ranging from 1.0 to 20.0 mols of hydrogen per mol of normally liquid hydrocarbon charge, the improvement which comprises increasing the yield of recoverable monocyclic aromatic hydrocarbons by introducing diphenyl into the reaction zone together with alkylated monocyclic aromatic-containing hydrocarbon fraction, said diphenyl being a relatively small amount as compared with total amount of normally liquid hydrocarbon charge to the reaction zone and recovering the monocyclic aromatic hydrocarbons.

3. A process according to claim 2 wherein said diphenyl is present in the feed in an amount ranging from about 1–5 mol percent based on total mols of normally liquid hydrocarbon charge to the reaction zone.

4. A process according to claim 2 wherein the rate of hydrodealkylation in the presence of said diphenyl compounds is maintained by the addition of a minor amount of $C_6$–$C_8$ paraffinic hydrocarbons to the charge.

* * * * *